United States Patent
Tsoukalis

(10) Patent No.: US 8,548,552 B2
(45) Date of Patent: Oct. 1, 2013

(54) IMPLANTABLE BIOSENSOR WITH AUTOMATIC CALIBRATION

(76) Inventor: Achilleas Tsoukalis, Anavyssos (GR)

( * ) Notice: Subject to any disclaimer, the term of this patent is extended or adjusted under 35 U.S.C. 154(b) by 558 days.

(21) Appl. No.: 12/720,334

(22) Filed: Mar. 9, 2010

(65) Prior Publication Data

US 2010/0228110 A1 Sep. 9, 2010

(30) Foreign Application Priority Data

Mar. 9, 2009 (GR) .................................. 090100135

(51) Int. Cl.
*A61B 5/05* (2006.01)

(52) U.S. Cl.
USPC ............................ 600/347; 600/345; 600/365

(58) Field of Classification Search
USPC ................. 600/365, 347, 345, 348, 349, 354, 600/396; 436/14; 604/504
See application file for complete search history.

(56) References Cited

U.S. PATENT DOCUMENTS

| 4,805,624 | A * | 2/1989 | Yao et al. ...................... 600/345 |
| 5,097,834 | A | 3/1992 | Skrabal |
| 5,503,630 | A * | 4/1996 | Ensminger et al. ....... 604/288.03 |
| 5,747,666 | A | 5/1998 | Willis |
| 6,495,352 | B1 * | 12/2002 | Brinker et al. ................ 435/176 |
| 2002/0027072 | A1 * | 3/2002 | Cui et al. ...................... 204/403 |
| 2003/0060753 | A1 * | 3/2003 | Starkweather et al. ......... 604/66 |
| 2003/0198558 | A1 * | 10/2003 | Nason et al. ..................... 417/53 |
| 2004/0133164 | A1 * | 7/2004 | Funderburk et al. .......... 604/134 |
| 2006/0211933 | A1 | 9/2006 | Zimmermann |
| 2006/0224129 | A1 * | 10/2006 | Beasley et al. ........... 604/288.01 |
| 2007/0208244 | A1 | 9/2007 | Brauker |
| 2007/0299617 | A1 * | 12/2007 | Willis .............................. 702/19 |
| 2008/0302659 | A1 * | 12/2008 | Sheppard et al. ........ 204/403.01 |
| 2009/0032394 | A1 * | 2/2009 | Wu et al. ........................ 204/400 |
| 2010/0266896 | A1 * | 10/2010 | Stromme et al. .............. 429/209 |
| 2011/0225112 | A1 * | 9/2011 | Cameron et al. ................ 706/20 |

FOREIGN PATENT DOCUMENTS

| EP | 1266625 | 12/2002 |
| WO | 00/59373 | 10/2000 |
| WO | WO 2008153395 A1 * | 12/2008 |

OTHER PUBLICATIONS

Zahn et al., An Integrated Microfluidic Device for the Continuous Sampling and Analysis of Biological Fluids, Proc. 2001 ASME Int'l Mechanical Engineering Congress & Exposition, Nov. 11-Nov. 16, 2001, pp. 1-6, New York, NY.

Yellambalase et al., Automated Oxidase-Coupled Amperometric Microsensor with Integrated Electrochemical Actuation System for Continuous Sensing of Saccharoids, Instrumentation & Measurement Technology Conf, pp. 1795-1800, Apr. 24-Apr. 27, 2006, Sorrento, Italy.

(Continued)

*Primary Examiner* — Michael Kahelin
*Assistant Examiner* — Tho Tran
(74) *Attorney, Agent, or Firm* — Duane Morris LLP; J. Rodman Steele, Jr.; Gregory M. Lefkowitz

(57) ABSTRACT

Implantable self-calibrating biosensor Subcutaneously or intracorporeally implantable biosensor, characterized by a closed microfluidic circuit with calibrating fluids, which communicates by a backward micro-dialysis logic with the exterior of said circuit, an open and in contact with the tissues and the interstitial fluid working electrode, for its self-calibration. One or more working electrodes may be positioned inside openable boxes from EAP, and be opened for the duration of the measurement and closed immediately after, succeeding one another in the measurement, as their sensitivity is diminished.

12 Claims, 5 Drawing Sheets

(56) References Cited

OTHER PUBLICATIONS

Moon et al., Microdialysis Glucose Sensor System Compared with Needle Type Glucose Sensor in Vivo During OGTT and Physical Exercise, IEEE Sensors 2006 Expo, Oct. 22-25, 2006, pp. 1000-1002, Daegu, Korea.

Zarkogianni et al., An Insulin Infusion Advisory System for Type 1 Diabetes Patients based on Non-Linear Model Predictive Control Methods, Proc. 29th Annual Int'l Conf of the IEEE EMBS, Aug. 23-26, 2007, pp. 5971-5974, Lyon, France.

* cited by examiner

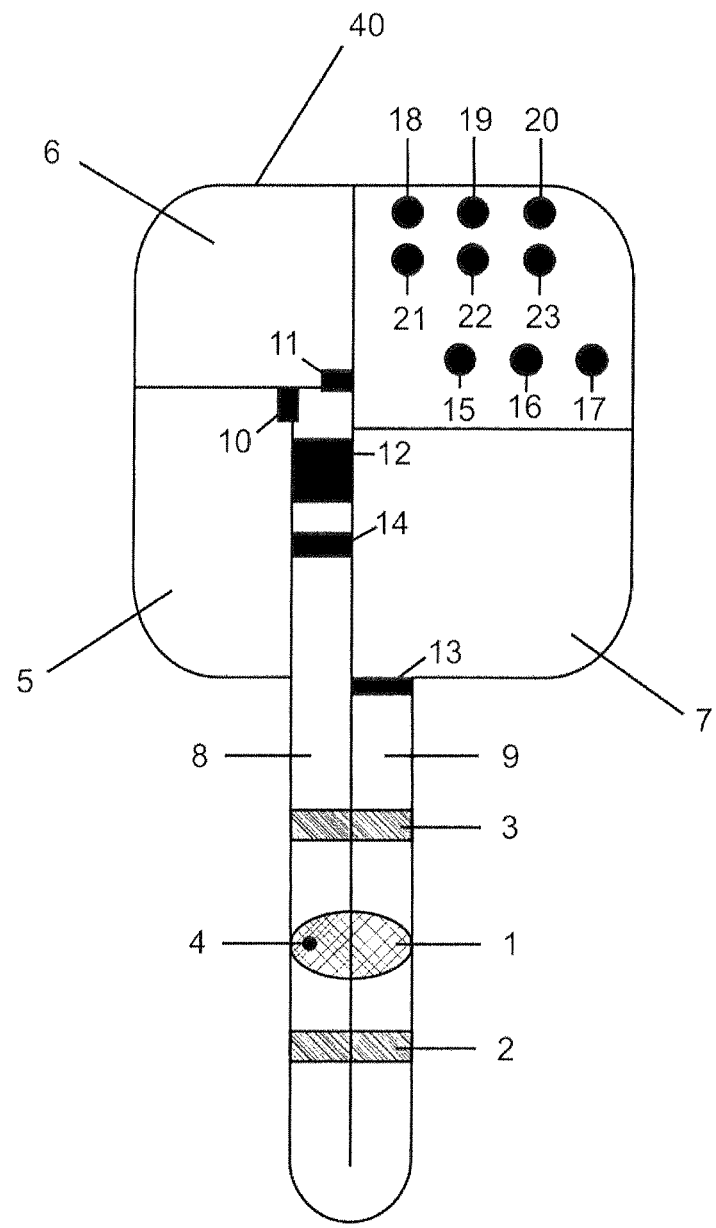
Fig. 1a/b

Figure 2B:
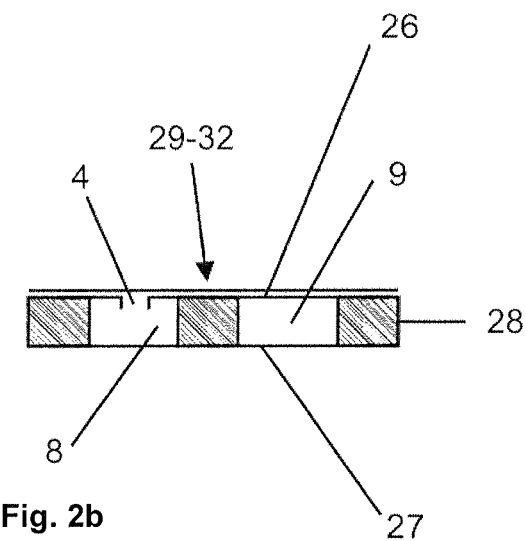
Figure 2C:
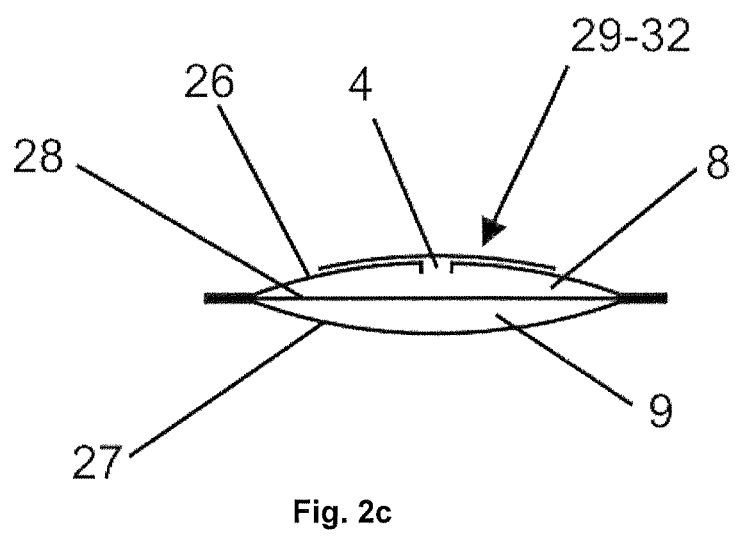
Figure 2D:
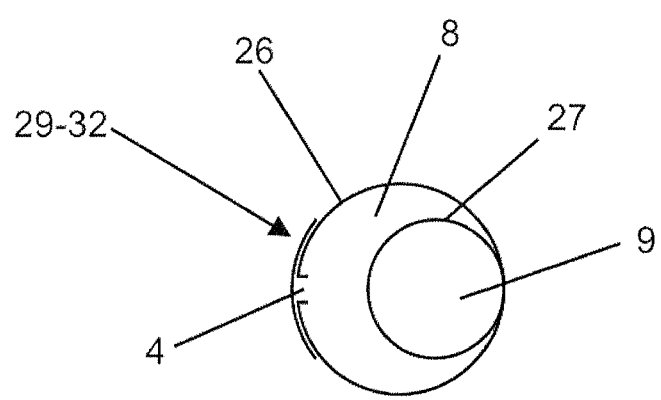

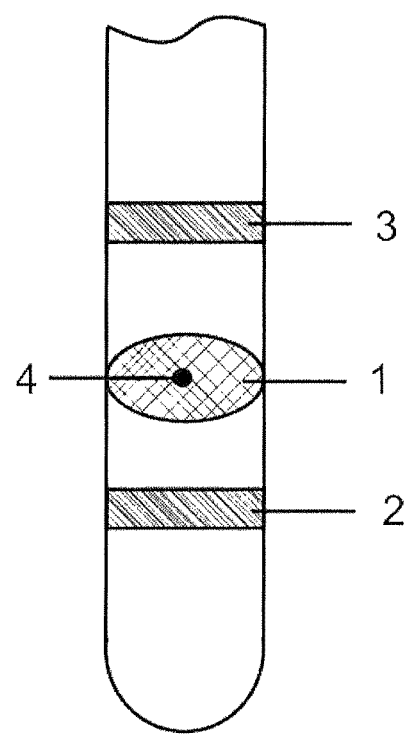
Fig. 1c/d
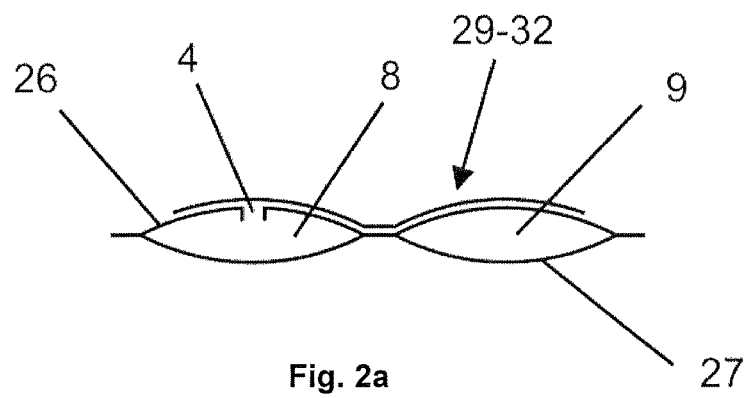
Fig. 2a

IMPLANTABLE BIOSENSOR WITH AUTOMATIC CALIBRATION

CROSS-REFERENCE TO RELATED APPLICATIONS

This application claims priority to Greek Application No. 20090100135, filed Mar. 9, 2009, which is hereby incorporated by reference.

BACKGROUND OF THE INVENTION

The need for biomedical sensors and in particular glucose sensors for preventing hypo-glycemic and hyperglycemic events in diabetics and for closed-loop controlling the insulin infusion via a portable or implantable pump is well known.

There are currently commercially available needle-like continuous measurement sensors, such as the Guardian & CGMS system of Medtronic company and another of Dexcom, and prior art US 2008/161666 to Feldman, U.S. Pat. No. 7,354,420 to Stell, U.S. Pat. No. 7,136,689 to Shults, but with a large error margin and a need for frequent calibration, 3-4 times daily with strips using a drop of blood (such as One Touch Ultra of LifeS-can Inc) by piercing of the finger.

Patents and patent applications such as Burton US 2003/0143746, Arvind US 2008/0234562, Korf U.S. Pat. No. 6,013,029, Lu Wang US 2007/0163894, disclose methods of self calibration, which are excellent for a large supply of glucose such as intravenously, but unsuitable for accurate interstitial measurements, where their use could result in a deficiency of the measured glucose due to the small available amount and to the small but substantial microdilution via dialysis. Additionally, the microdilution measurements are delayed, and their accuracy depends on the accuracy of the flow rate of the circulating liquid and the stability of the temperature.

In the patent application «Nanostructured composite material and biosensor containing same» GR2008100409 (Chaniotakis), an enhanced form sensor which has a long life-span against in vivo erosion is presented, although it lacks self calibration, which is essential for the reliability of closed-loop injections—an autonomous robotic system.

The need for a fully implantable artificial pancreas with simultaneous glucose measurement and robotic insulin infusion is known, but the presently available technologies do not meet the need for a reliable, and longlasting accurate measurement.

In the continuous measurement with a needle-like sensor in the subcutaneous tissue, the measurement of glucose differs from that of blood with time-delay and a different standard. Algorithms that are known through the relevant literature have been developed using neural networks and other methods (Mougia-kakou, A. Prountzou, D. Iliopoulou, et al. Nikita, A. Vazeou, C. S. Bartsocas, "Neural Network based Glucose—Insulin Metabolism Models for Children with Type 1 Diabetes," Engineering in Medicine and Biology Conference 2006 (EMBC '06), IEEE, New York City, USA, September 2006, & Mougia-kakou, K. Prountzou, et al. Nikita, "A Real Time Simulation Model of Glucose-Insulin Metabolism for Type 1 Diabetes Patients," Engineering in Medicine and Biology Conference 2005 (EMBC '05), IEEE, Shanghai, China, September 2005) with which we can predict the blood glucose at the instant of the subcutaneous measurement and 30 minutes later.

Yellambalase et al presented at the IMTC 2006 (Instrumentation and Measurement Technology Conference, Sorrento, Italy 24-27 Apr. 2006) a needle-type biosensor system with fully automated operations, in which an oxidase-coupled amperometric sensor with an oxygen depleting/generating actuator is interfaced with an electrochemical instrument and a perfusion system.

Microfluidic capillary blood absorption lumens are known in the art, in strip type glucose sensors, see Cul US 2006/0175205, Karinka U.S. Pat. No. 6,863,800, Say US 2008/167543.

It is also known that glucose penetrates microporous nanostructures, such as a nanofiber matrix with embedded glucose oxidase receptor (GOX) and an overcoat of a biomimetically-composed matrix film of silicon oxide, see the patent application with the priority GR2008100409 (Chaniotakis).

It is an intention of the present invention to provide a method for a reliable, accurate measurement of biomedical parameters with self-calibration and the prediction of blood glucose for the timely information of the user and the medical assessment and for the automatic closed-loop insulin infusion.

BRIEF DESCRIPTION OF THE INVENTION

The present invention is a hybrid implementation of a dialysis circuit arranged in the interior of a needle sensor, the dialysis circuit being used only for calibration, with sensor calibrating fluids (liquids and/or gases) circulating in a closed microfluidic circuit, and of two or three conducting regions in the exterior of the sensor, as is known for enzymatic sensors, in contact with the body, wherein the layers of the working electrode are in fluid communication with the interior microfluidic circuit through an opening, in a novel backward microdialysis device. The enzyme measures what there is in excess, if there is a posterior supply it measures the posterior concentration, if the posterior flow is stopped, it measures the anterior body concentration. The measurement, after the calibration procedure, may preferably be effected exactly as disclosed in the patent application with the priority GR2008100409 (Chaniotakis), as in a standard subcutaneously implantable sensor.

The present invention predicts hyperglycemia and hypoglycemia, thus enabling the patient to have time to react before it is too late, since presently in some cases, the patient is conscious, but immobilized without being able to react.

The present invention provides the technical and operational ability to completely implant the sensor, solving the problem of the consumption of the enzyme, and with telemetric transfer of data from and to the body. The present invention also solves the problems of constructing an artificial pancreas, both at the level of closed-loop algorithms and at the level of securely transporting fluids from and to the body.

BRIEF REFERENCE TO THE DRAWINGS

FIGS. 1A-D show front views of the preferred embodiments A-D of the disposable (needle).

FIG. 2A-E show a section of the sensor at the level of the working electrode, especially the junction of two (A) or three (B-C) films or tubes (D) for constructing two microfluidic lumens 8, 9 and (E) a section of a completed dual lumen tube.

Figure 3:
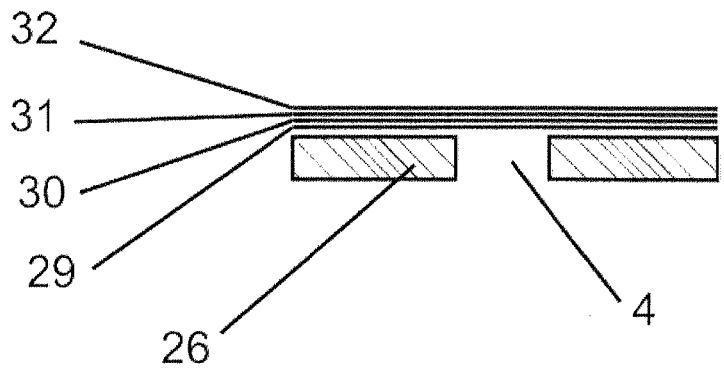

FIG. 3 shows the layers of the working electrode above the diffusion hole.

Figure 4A:
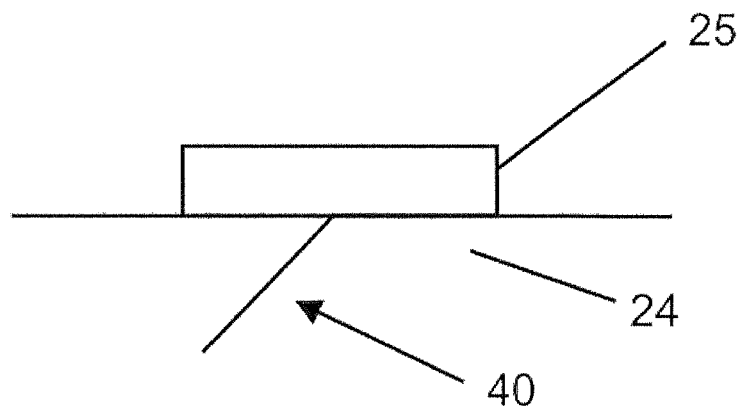

FIGS. 4A and B show the complete continuous measurement sensor, the extracorporeal part of the sensor and the electronic control in contact therewith, with the implanted needle folded 4A or extended 4B.

Figure 5:
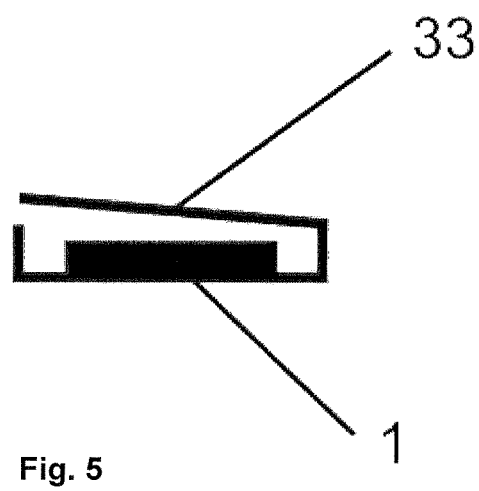

FIG. 5 shows a working electrode in a waterproof microbox with openable lid.

DETAILED DESCRIPTION OF THE INVENTION

The present invention uses a disposable needle-sensor (FIG. 1) implantable subcutaneously through its small width part, while the larger width part contains bags, a pump and electric contacts. The sensor in its disposable, needle-like part is of microscopic width and thickness, consisting of an external surface in contact with the body, and of descending and ascending lumens internally to the needle, forming a hydraulic microfluidic circuit, through which pass the fluids for calibrating the sensor. The microfluidic circuit transports fluid down to the level of the working electrode from the input lumen 8 and from there it short-circuits with the output lumen 9 and passes to the drain vessel 7, as is known for microdialysis devices.

The so-called microfluidic circuit, in a preferred embodiment (FIG. 2A), can consist of two insulating layers 26, 27, impermeable to liquids or gases, of a material such as a plastic sheet, which constitute, with the proper, use such as by mechanical junction or laser bonding or with a third layer of material 28 (FIG. 2B) as in the above patents, a microfluidic circuit 8, 9.

In another embodiment (FIG. 2C), the microfluidic circuit can consist of three films 26, 27, 28 which, joined at the edges, create an anterior lumen 8 and a posterior lumen 9 between first-second and second-third film. The intermediate film is cut or pierced at the level of the working electrode for the necessary short-circuit between cathode and anode. The first film 26 comports externally the measuring electrodes 1, 2, 3.

In another embodiment (FIG. 2D), the microfluidic circuit can consist of two lumens 8, 9 inside of each other and joined externally along an edge, and the exterior can be closed at the distal end. Also, the exterior lumen comprises the measuring electrodes.

In another embodiment (FIG. 2E) the microfluidic circuit consists of a double-lumen plastic biocompatible needle of 0.33 mm in external diameter (an approximately 30G needle) such as those manufactured by Microspec 4 Corporation Petersborough, N.H., USA, which is hydraulically and mechanically connected with an extracorporeal part manufactured by micromolding, which contains the pumping system, micro-fluidic lumens and the calibrating/draining fluid bags.

At the external surface of the sensor in the above preferred embodiments, there are conductive material lanes made using the thin film technology (Method of fabricating thin film sensors U.S. Pat. No. 5,391,250), or thick film coating such as the "micropenning technology" of very small dimensions, of Micropen Technologies New York USA. The so-called lanes are: The surfaces of the three electrodes 1, 2, 3 on the measuring needle from precious metals or carbon and/or silver as detailed below, the signal transport conductors in the extracorporeal part up to the contacts 15, 16, 17 for the electronic part, and the pump valve contacts 18-23 with the conductor lanes up to the valves 10-14. The conductive coating is overcoated, wherever needed, with an insulating film. In particular, there are micro-surfaces on the exterior of the needle as above for the two or three measuring electrodes 1 (working electrode, carbon or platinum), 2 (counter electrode, gold), 3 (reference electrode, Ag/AgCl) as is known from the conventional glucose oxidase measurement and the corresponding contacts 17, 15, 16 for the constant part containing the electronics. Alternatively a ferrocyanide/carbon working electrode may be used, preferably in combination with a carbon counter electrode and a silver reference electrode. Alternatively other low curing temperature conductive electrodes can be used.

In particular (FIG. 3), in the microfluidic system of the present invention the carbon or ferrocyanate/carbon or platinum 29 of the working electrode 1, but also the plastic wall 26, have a microsurface allowing for diffusion, which may comprise a central microhole 4. The central microhole 4 may be made by laser, microdrilling or another method, after the deposition of the metal electrodes but before the layering of the working electrode with the nanomaterials 30-32 for glucose measuring. Alternatively the microsurface allowing for diffusion may comprise a layer 26 which is eroded in the area behind the working electrode layers 29-32 in order to become porous, or a conventional microdialysis membrane is applied in the area of layer 26 behind the working electrode layers 29-32. A hole that pierces or extends through the layers 29-32 (although the extension of the hole 4 through the layers 29-32 is not depicted in FIGS. 2 A-E and 3) and other diffusive topologies will be referred, for the purposes of the present invention, as a "hole".

The inventive operation of the above hole 4 is such that the calibration fluids circulating in the microfluidic circuit 8, 9 wet the rear side of the laminate nanomaterial (FIG. 3) made of nanofibers 30, nanofibers comprising immobilized Glucose oxidase (Gox) 31, biomimetically synthesized biosilica membrane 32 as described in the patent application having the priority GR2008100409 (Chaniotakis), which is applied above the platinum or carbon disk 29 of the working electrode 1 and covers the communication hole 4 which is in communication with the rear closed microfluidic circuit 8. Other simpler electrode chemistries may also be used to minimize costs. With the same ease that glucose in the interstitial space penetrates this layering from the anterior part and is measured by the two or three electrodes 1, 2, 3 using a potentiostat instrumentation as is known in the art, the calibration fluids penetrate inversely, from rear to front through said hole or microhole 4 by osmotic pressure proportionally to the concentration differential. The system is a hybrid of a backward microdialysis device in the interior side with replacement of the conventional diffusion membrane by the layering of nanomaterials (FIG. 3) of the working electrode, and of a conventional needle-like sensor in the exterior side (FIG. 1). The technique is referred as backward microdialysis because diffusion proceeds to the exterior, where the measuring system is located, in contrast with the conventional microdialysis wherein biological fluids diffuse towards the circulating fluid and the measurement takes place inside the closed hydraulic circuit. The calibrating fluids may be one or more glucose concentrations (bag 6), preferably in injectable form since it is known that glucose is not stable with time, alternating with wash fluid (bag 5) without any glucose, preferably consisting of deionized water, buffer, surfactants, and preservatives. Those fluids are stored in micro-bags 5, 6 on the exterior extracorporeal part of the disposable enlarged section of the sensor. For the circulation of those fluids are preferably employed the noiseless, low cost and good linearity and low consumption electroactive polymers (EAP), such as those sold by Artificial Muscles, Inc. Sunnyvale, Calif. in three-finger configuration 10 or 11 fluid selecting valves working as input valves, a fluid transport finger 12, and an output valve 14 as a conventional peristaltic finger valve 3, wherein the optional finger 13 prevents the downflow of the fluid to the drain 7, alternatively a piston pump may be used, with two passive or active valves by micromolding. Alternatively, piezoelectric pumping devices and valves may be employed, such as those of Bartels Mikrotechnik GmbH., Dortmund, Germany, or electrostatic pumps such as MEMS chips.

Alternatively for pumping may be used the pumping methods disclosed in U.S. Pat. No. 6,013,029. The amounts needed are of the order of a few microliters and the whole system is particularly miniaturized.

The calibration procedure is similar to the prior art (Arvind US2008/0234562) sequence of three calibration fluids, with the exception constituting the inventive step that for the main glucose measurement, the calibration fluid is the last aqueous buffer that remains immobile during the intervals between calibrations.

During calibration, the glucose excess arrives rapidly from the rear and the measurement of the upper calibration point is fast, despite the low diffusion of glucose to the interstitial fluid. That is, due to the subsequent next calibration step depletion of intersticial fluid glucose backwards in the water of the micro-fluidic circuit, the body glucose penetrates the layers of the sensor to the rear, and the delay to deplete glucose in the interstitial fluid and to lower the concentration is small. The sensor "sees" this as an asymptotic curve tending to zero, and from the corresponding mathematical analysis calculates the theoretical zero. The glucose concentration of the patient is not affected by this calibration procedure because of two reasons. On one hand a very low amount is transported towards and from the body, this low amount being controlled by the size of the hole 4 and the density of the layers 29-32 of the sensor working electrode; and the increased level of glucose in the body due to the first glucose solution is cancelled by the subsequent lowering due to the second aqueous fluid. On the other hand the glucose concentration of the patient is not affected because the entire calibration procedure only lasts for a few seconds. The back fluid does not affect the main measurement, since it is situated behind the enzyme. The only negative effect achieved is that glucose continues to penetrate through the nanofibers to the back lumen until the concentrations are equilibrated, which is realized very rapidly, in one second, according to theory (diffusion time=$x^2 D$ wherein x=diffusion distance and D=diffusion constant $6.7 \times 10\text{-}6$ cm$^2$/sec for glucose in a low viscosity fluid such as water). Moreover, in most of the proposed embodiments of the invention, the plastic sheets or the elastic tubes are reconnected by the pressure of the body tissues, if there is no circulating fluid (pump stopped without circulation during the most part of the main measurement) and thus there is no back fluid during the main measurement or the concentration of the fluid is equilibrated.

In a preferred embodiment of the present invention behind the hole 4 of the sensor wall 26 to the microfluidic channel 8, a miniature sub millimeter valve is arranged capable of closing the hole 4 from inside the microfluidic channel. The valve remains closed during normal measurement and opens during calibration, to prevent penetration of calibrating fluids through the hole during normal measurement after calibration. This type of angled valve is produced e.g. by Micromuscle AB.

The disposable part of the invention is similar to that of the Feldman patent application US 2008/01161666, but the extracorporeal part also contains the pumping systems 12, 14 with the valves 10, 11, the calibration fluid 5, 6 and drain 7 vessels, the ends of the input 8 and output 9 lumens, in the vessels 5 or 6 and 7 respectively, and the two or three contacts of the electrodes 15, 16, 17, together with the contacts of the linear actuators EAP 18-23 (five digital inputs, equal to the fingers plus ground—GND).

Figure 2E:
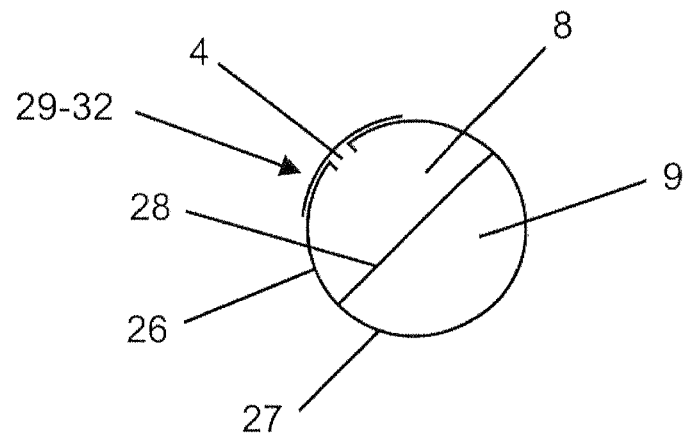
Figure 4B:
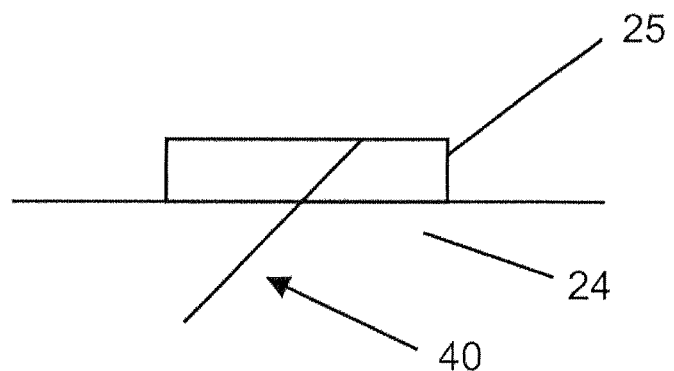

FIG. 4 shows the extracorporeal part of the sensor, and electronic control in touch with it, and the implantable plastic needle 40. The needle 40 may be either angled (FIG. 4A) or straight (FIG. 4B), i.e. the needle can be straight within the embodiment as shown or bended—horizontal then angled. In FIGS. 4A and 4B, numeral 24 denotes the body under the skin, where the glucose concentration of the interstitial fluid is measured. Numeral 25 refers to the disposable sensor including electronics or plus electronics on top. Numeral 40 refers to the needle (as shown in the bottom of FIGS. 1A/B) having microfluidic channel 8/9 in its interior (see sectional view of FIGS. 2A-E) and externally the electrodes (FIG. 2E or FIG. 1 C/D).

The permanent, non-disposable electronic part of the sensor contains an analog or combined analog and digital potentiostat as is known, Wang US 2007/0163894, and the processing section, together with telemetry, according to patent U.S. Pat. No. 7,161,484 to Tsoukalis, preferably Blue Tooth Low Energy (BLE) Continua protocol for an open system or Nordic Semiconductor ANT ultra low power embedded protocol for a closed system to others. The measurements are preferably collected in a mobile collecting and data broadcasting system with a permanent TCP/IP connection (through GPRS or WiFi or WiMax) such as the commercially available UP-Connect and server from Micrel Medical Devices, Athens, Greece.

The system may be powered by a battery, rechargeable battery, rechargeable battery through magnetic waves (low frequency RF), or by pumping energy (energy harvesting) from the body glucose and other methods known in the art.

The processing section comprises neural networks capable of processing the glucose measurement in the subcutaneous tissue taking into account the insulin injection; and a prediction of blood glucose concentration is output, current and 30 minutes, for triggering alerts. The processing section preferably contains means capable of running the predictive algorithms of blood glucose according to the numerous above publications as known in the art, in such a way that we can use the current value in closed-loop injection algorithms, and the 30 minutes prediction for alerting the user of an imminent hyperglycemia or hypoglycemia and, through the long range system (GPRS) to notify the attending doctor and the ambulance. The glucose measurement, the insulin injection and the uptake or consumption through exercise of carbohydrates and lipids are employed for the prediction.

Preferably the processing section comprises means for current glucose prediction wherein those means allow for algebraic addition of the concentration prediction by means of the kinetics of meal digestion and of the prediction of the consumption kinetics during and after exercise, to obtain a global blood glucose concentration prediction for triggering alarms and calculating the closed-loop injection. Further preferably the processing section comprises means for feeding differences between the predicted blood glucose value and the desired glucose value to a PID (proportional/Integral/Differential) algorithm to obtain the corresponding insulin injection correction and the robotic (closed loop) insulin injection correction.

In case of closed-loop injection/measurement, the interconnection between sensor and pump may be effected by cable or the cable may be used in a bad interconnection alert. The closed-loop system, part of which is the sensor of the present invention, is composed of the present glucose sensor with means for the prediction of current blood glucose concentration, the insulin pump containing both means for closed-loop algorithms and conventional software as an alternate safety measure (plan B) in the event of an interconnection error, and a real time program through said local or long range telemetry system. The injection algorithm comprises:

data entry:
previous value of insulin injection rate of the pump (output $R_{n-1}$),
prediction of blood glucose of the sensor of the present invention, algorithmic prediction of additional glucose to the blood per minute (digestion and work metabolism kinetics) after informing the system of meals or exercise by means of the above handheld mobile application system, that corrects the above prediction of the present sensor due to external parameters that cannot be correctly predicted exclusively by the rate of change of glucose,
other known information about the patient from data bases deriving from the server through the internet,
PID algorithm known in the art (U.S. Pat. No. 7,354,420) for processing the above processed data and calculating corrections and data output:
the current insulin injection rate of the system's pump $R_n$.

Preferably the biosensor comprises a mechanical introducer for the implantation. The sensor is implanted using an introducer similar to the prior art (Funderburk US2004/0133164), and the non-disposable part which has electric contacts with the mobile part, is fixed to the skin with self-adhesive, for this reason the whole non-disposable part is particularly miniaturized.

The present invention is appropriate for an implantable sensor or a combination of insulin pump-sensor (artificial pancreas) with the addition of removable lids 33 (FIG. 5) of electroactive polymers (EAP), such as those in www.micromuscle.com to a plurality of sensors, wherein each sensor opens its lid for a measurement and closes it immediately after that for minimizing the enzyme erosion. Thus the present invention includes an implantable device comprising a plurality of biosensors comprising at least one biosensor of the type described above wherein each sensor comprises a lid, preferably of electroactive polymers. The lids are capable of exposing only the currently active sensor for a short interval, necessary for a measurement or a calibration and closing just after the measurement or calibration to protect the enzyme from erosion, while the others remaining hermetically closed and wherein said lids can have a protective filter to avoid the introduction of larger than desired particles or molecules. In this way the lifetime of the sensor increases from one month, as reported in the patent application having the priority GR2008100409 (Chaniotakis), to one year by being used only for a few minutes daily in total. The present invention constitutes an inventive step compared to the patent applications of the Microchips company, Scott US 2009/030404, Santini US 2008/11536, where the exposure of the various sensors is effected by electro-erosion and thus the sensor cannot be covered again for protection when exposed. In the present invention, when a sensor shows a low sensitivity during the calibration, it is disconnected and replaced by another neighboring one which is closed up to that moment. Thus, a small number of sensors can maintain an active measurement for many years, which is essential for an implantable instrument.

In the implantable device the self-calibration is maintained. To achieve that, a transdermal needle is needed to fill the subcutaneously implanted artificial pancreas with holes at various heights, for the respective vessels disposed at different heights, filling with insulin, aqueous buffer, calibration and corrective injection glucose solution, and removing the drained fluid. The fluid transport is made by a special transport pump comprising position sensors in order to assess the correct position of the multiple fluid transport needle and to avoid a deleterious injection in the body. The transport of fluids is made automatically possible only after validating the correct position, and stops if a sensor signals a problem.

Preferably the implantable artificial pancreas comprises
a sensor as described above
means for closed-loop injection algorithms,
vessels for insulin, aqueous buffer, calibration and corrective injection glucose solution, those vessels being arranged at different heights, the vessels being elastic or collapsible bags,
insulin-injection dual pumps effecting the transport of insulin injection and calibration fluids and the drainage of calibration wastes.

In a preferred embodiment the implantable artificial pancreas comprises a filling pumping system comprising a multilumen catheter which has at its end a needle (more specifically, a multiple fluid transport needle) with position sensors for assessing the correct position of the needle, the multilumen having holes at various heights provided with valves allowing for communication with the vessels of the artificial pancreas and interruption of the fluid transport from and toward the artificial pancreas in the event of the identification of an error by said sensors.

The above-described filling pumping system can also be used for purposes independent of the implantable artificial pancreas of the present invention.

The invention claimed is:

1. Self-calibrating disposable biosensor comprising an electronic part and an electrochemical part, wherein the electrochemical part comprises
    a needle having an external surface configured to contact living tissue, said needle having in its interior a microfluidic circuit (8, 9) for the circulation of at least one calibration fluid, and
    two or three electrodes (1, 2, 3) arranged on the external surface of the needle, one of the electrodes being a working electrode (1), said working electrode comprising porous bio-chemical sensing materials (30-32) configured to contact living tissue after implantation, and
    means for fluid communication (4) of the microfluidic circuit (8,9) for the calibration fluid which is in the interior of said needle with the layers (29-32) of the working electrode on the external surface of the needle.

2. Biosensor as in claim 1, wherein a disposable nonimplantable extracorporeal part (40) comprises bags (5,6) with or without a protective cover, the bags containing calibration and draining fluids; a drain vessel (7); and pumps; flow control valves; and contacts with the electronic part for both the measurement and control of the calibration micro flow.

3. Biosensor as in claim 1 for measuring glucose, wherein the working electrode (1) comprises a conductive base made preferably of carbon or ferrocyanide/carbon or platinum or gold (29), nanofibers (30) with embedded immobilized glucose oxidase (31) and a coating of biomimetically synthesized silicon dioxide matrix (32).

4. Biosensor as in claim 1, further comprising pumping fingers and valves (10-14) for intermittently circulating one or more glucose solutions and fluids without glucose within the interior microfluidic circuit (8, 9) for self-calibration of the biosensor.

5. Biosensor as in claim 1, further comprising pumping fingers and valves (10-14) comprising electroactive polymers, said pumping fingers and valves (10-14) configured for pumping of the microflow and selection of a circulating fluid.

6. Biosensor as in claim 1, wherein the electronic part comprises a processing section comprising neural networks capable of processing a glucose measurement in the subcutaneous tissue taking into account insulin injection and of putting out a prediction of current venal blood glucose concentration and of venal blood glucose concentration after 30 minutes for triggering alerts.

7. Biosensor as in claim 6, wherein the processing section comprises means for current glucose prediction, those means allowing for algebraic addition of the concentration prediction by means of the kinetics of meal digestion and of the prediction of the consumption kinetics during and after exercise, to obtain a blood glucose concentration prediction for triggering alarms and calculating closed-loop injection.

8. Biosensor as in claim 7, wherein the processing section comprises means for transmitting differences between the predicted blood glucose value and the desired glucose value preferably to a PID (proportional/integral/Differential) algorithm to obtain a corresponding insulin injection correction and a robotic (closed loop) insulin injection correction.

9. Biosensor as in claim 1 further comprising a mechanical introducer for the implantation.

10. Implantable device comprising a plurality of biosensors comprising at least one biosensor according to claim 1, wherein each sensor comprises a lid, the lids being capable of exposing only the currently active sensor for a short interval, necessary for a measurement or a calibration and otherwise remaining closed, while the other sensors remaining hermetically closed till replacing the active sensor and wherein said lids can have a protective filter to avoid the introduction of larger than desired particles or molecules.

11. Implantable artificial pancreas comprising
a sensor according to claim 1,
means for closed-loop injection algorithms,
vessels for insulin, aqueous buffer, calibration and corrective injection glucose solution, those vessels being arranged at different heights, the vessels being elastic or collapsible bags, and
insulin-injection dual pumps effecting the transport of insulin injection and calibration fluids and the drainage of calibration wastes.

12. Biosensor as in claim 1, comprising bag pumping and measuring electronics, wherein the bag pumping and measuring electronics comprise microelectromechanical systems (MEMS) circuit, an electromechanical autonomous circuit, or a combination of both.

* * * * *

UNITED STATES PATENT AND TRADEMARK OFFICE
CERTIFICATE OF CORRECTION

| | | |
|---|---|---|
| PATENT NO. | : 8,548,552 B2 | Page 1 of 1 |
| APPLICATION NO. | : 12/720334 | |
| DATED | : October 1, 2013 | |
| INVENTOR(S) | : Achilleas Tsoukalis | |

It is certified that error appears in the above-identified patent and that said Letters Patent is hereby corrected as shown below:

In the Claims

In column 8, line 47, of claim 2, the word "and" should be deleted prior to the word pumps In column 8, line 52, of claim 3, the word "preferably" should be deleted In column 9, line 1, of claim 6, please insert the word --an-- after the word account Signed and Sealed this
Twentieth Day of May, 2014

Michelle K. Lee
*Deputy Director of the United States Patent and Trademark Office*